United States Patent [19]

Moore et al.

[11] Patent Number: 5,149,821

[45] Date of Patent: Sep. 22, 1992

[54] PROCESS AND INTERMEDIATES FOR OPTICALLY ACTIVE 3-FORMYLTETRAHYDROPYRANS

[75] Inventors: Bernard S. Moore; Frank J. Urban, both of Waterford, Conn.

[73] Assignee: Pfizer Inc, New York, N.Y.

[21] Appl. No.: 596,165

[22] Filed: Oct. 11, 1990

[51] Int. Cl.⁵ .................................. C07D 263/02
[52] U.S. Cl. ....................................... 548/215
[58] Field of Search ........................... 548/215

[56] References Cited

U.S. PATENT DOCUMENTS 2,852,427  9/1958  Eden .................................. 548/215
3,896,141  7/1975  Keck et al. ........................ 548/215

OTHER PUBLICATIONS

Kelly, R. et al., Tetrahedron Letters, 19, pp. 1709-1712 (1973).

*Primary Examiner*—C. Warren Ivy
*Assistant Examiner*—Raymond Covington
*Attorney, Agent, or Firm*—Peter C. Richardson; J. Trevor Lumb; Gregg C. Benson

[57] ABSTRACT

Process and intermediate useful in the preparation of optically active 3-formyltetrahydropyrans from racemic 3-formyltetrahydropyran.

8 Claims, No Drawings

PROCESS AND INTERMEDIATES FOR OPTICALLY ACTIVE 3-FORMYLTETRAHYDROPYRANS

BACKGROUND OF THE INVENTION

The present invention is directed to a process and intermediates for the preparation of optically active 3R-formyltetrahydropyran (alternatively named tetrahydropyran-3R-carboxaldehyde or tetrahydropyran-3R-carbaldehyde), of the absolute stereochemical formula

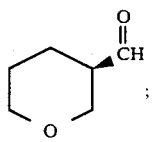
(Ia)

and its enantiomer, of the absolute stereochemical formula

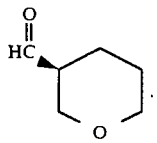
(Ib)

These optically active aldehydes are employed as precursors in the preparation of certain valuable optically active benzoxazolone derivatives of the formula

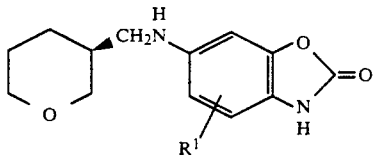

and the corresponding enantiomeric compounds, wherein $R^1$ is hydrogen, $(C_1-C_3)$alkyl, $(C_1-C_3)$alkoxy, phenoxy, $(C_1-C_3)$alkylthio, phenylthio, halo or trifluoromethyl. These compounds are also disclosed in commonly assigned and copending U.S. patent application Ser. No. 07/529,971, filed May 29, 1990 now U.S. Pat. No. 5,086,052. These compounds, by inhibiting certain lipoxygenase and cyclooxygenase enzymes, are of particular value in the treatment of allergic and inflammatory conditions in mammals.

The optically active aldehydes (Ia) and (Ib) are quite unstable, being readily racemized under mildly basic or acidic conditions via achiral intermediates. They were heretofore prepared by a multistep process from R-malic and S-malic acid, respectively. The present invention provides a highly efficient process for these optically active aldehydes which employs exceptionally mild, non-racemizing conditions in their isolation.

Diastereomeric oxazolidine derivatives of (+)-ephedrine have been previously employed in the optical resolution of certain aldehydes which are used as intermediates in the synthesis of prostaglandins. Kelly et al., Tetrahedron Letters, pp. 1709-1712, 1973.

SUMMARY OF THE INVENTION

The present invention is directed to a process for the preparation of optically active 3R-formyltetrahydropyran (of the formula Ia above) or 3S-formyltetrahydropyran (of the formula Ib above), which comprises the steps of:

(a) reacting racemic 3-formyltetrahydropyran in a reaction inert solvent either with (+)-ephedrine to form a mixture of diastereomeric oxazolidines of the formulas:

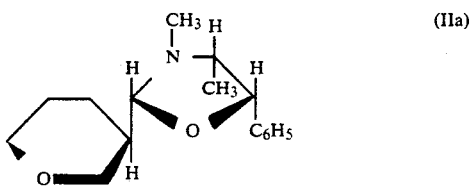
(IIa)

and

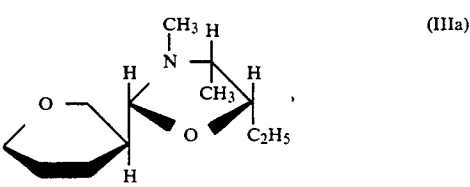
(IIIa)

or with (−)-ephedrine to form a mixture of diastereomeric oxazolidines of the formulas:

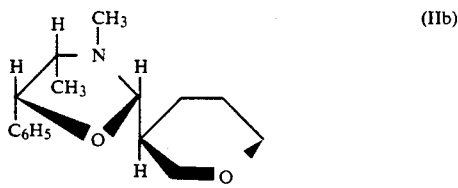
(IIb)

and

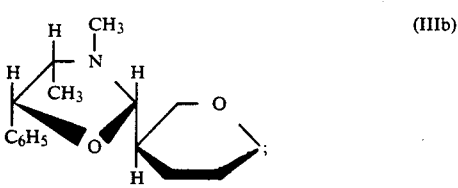
(IIIb)

(b) separating the diastereomeric oxazolidine of the formula (IIa) or (IIb) from its respective mixture in the form of a crystalline, acid addition salt; and (c) hydrolyzing in water the resulting diastereomeric salt of the oxazolidine of formula (IIa) or (IIb) to form, respectively, said optically active 3-formyltetrahydropyran of the formula (Ia) or of the formula (Ib).

The present invention is also directed to 3, 4R-dimethyl-5S-phenyl-2R-(3R-tetrahydropyranyl) oxazolidine (of the formula (IIa), depicted above), 3,4S-dimethyl-5R-phenyl-(2S-(3S-tetrahydropyanyl) oxazolidine (of the formula (IIb), depicted above), and to their acid addition salts. The detailed structure showing the cis-relationship of the tetrahydropyranyl group with the 4-methyl and phenyl substituents in these compounds was shown by an X-ray crystallographic analysis carried out by Dr. Jon Bordner.

Because of their ready separation from corresponding salts of the undesired diastereomeric oxazolidines, the preferred acid addition salts of the compound (IIa) are those formed with 1S-camphorsulfonic acid or with p-toluenesulfonic acid. In the case of the compound (IIb), salts with 1R-camphorsulfonic acid or with p-toluenesulfonic acid are preferred.

DETAILED DESCRIPTION OF THE INVENTION

The present invention is readily carried out. In the variation directed to the preparation of 3R-formyltetrahydropyran (of the formula Ia above), racemic 3-formyltetrahydropyran is reacted with substantially one molar equivalent of (+)-ephedrine (alternatively named 2R-(methylamino)-1S-phenylpropanol) in a reaction inert solvent to form a 1:1 mixture of diastereomeric oxazolidines of the formulas (IIa) and (IIIa) as depicted above. The temperature used for this reaction is not critical. Generally, ambient temperature (e.g., about 15°-30° C.) is used so as to avoid the cost of heating or cooling. As used in this paragraph, and elsewhere herein, the expression "reaction inert solvent" refers to a solvent which does not interact with starting materials, reagents, intermediates or product in a manner which would adversely affect the yield of the desired product. Reaction inert solvents particularly well suited for the present interaction of racemic aldehyde with (+)-ephedrine are those which form part or all of the solvent system from which an acid addition salt of the desired diastereomer will crystallize while leaving the undesired diastereomer in solution. Thus, when either p-toluenesulfonic acid or a camphorsulfonic acid is used to form the acid addition salt, the desired isomer crystallizes particularly well from 1:1 $CH_2Cl_2$: isopropyl ether. Thus one or the other, or a combination of $CH_2Cl_2$ and isopropyl ether find preferred use in the initial reaction of the racemic aldehyde with (+)-ephedrine. Most preferred as the initial solvent is $CH_2Cl_2$, with isopropyl ether added at such time as the desired enantiomeric camphorsulfonate or toluenesulfonate salt is to be crystallized.

When 3S-formyltetrahydropyran is the desired product, (−)-ephedrine is substituted for (+)-ephedrine, and 1R-camphorsulfonic acid for 1S-camphorsulfonic acid in this process.

Water is a by-product in the reaction of racemic 3-formyltetrahydropyran with ephedrine. So as to force the reaction to completion, and avoid the reverse reaction of hydrolysis, it is preferred to use some means of removing water from the reaction mixture. This is readily accomplished by adding a drying agent (e.g., anhydrous $MgSO_4$, a molecular sieve) or by azeotropic distillation (e.g., with benzene or toluene), preferably at reduced pressure.

At such time as it is intended to crystallize the desired acid addition salt, the composition of the solvent is adjusted as desired and the reaction mixture is contacted with at least 0.5 molar equivalent (usually up to about 1 molar equivalent) of the appropriate acid. A large excess of acid is generally avoided, since the common ion effect will tend to cause co-precipitation of the salt of the undesired diastereomer.

If desired the salt of the diastereomeric oxazolidine is converted to its free base form. This is best accomplished by exposing the salt to a mild base, such as $Na_2CO_3$, in a two phase aqueous/organic solvent system in which the free base, by its immediate extraction into the organic solvent, receives minimal exposure to water.

It is generally preferred, however, to convert the salt of the diastereomeric salt (IIa) or (IIb) directly to the desired optically active aldehyde (Ia) or (Ib). This conversion is readily accomplished without racemization by simply exposing the acid addition salt to water. The hydrolysis reaction, which is conveniently carried out at ambient temperature, can usually be monitored by pH. For example, the 1S-camphorsulfonate salt of (IIa) in water shows an initial pH of about 3.2 which rises to a steady value of about 4.3 when hydrolysis of the oxazolidine to aldehyde is complete.

The racemic 3-formyltetrahydropyran used as starting material is readily available via hydrogenation of 3-formyl-5,6-dihydro-2H-pyran as exemplified below. Typical use of optically active 3-formyltetrahydropyrans in the synthesis of 6-[(3S- and 3R-tetrahydropyranyl)methylamino]-2(3H)-benzoxazolone derivatives is also exemplified below.

The derived benzoxazolone compounds of the formula (IV) depicted above and their enantiomers inhibit the activity of the lipoxygenase and/or cyclooxygenase enzymes. This inhibition has been demonstrated by an assay using rat peritoneal cavity resident cells which determines the effect of said compounds on the metabolism of arachidonic acid. The ability of these compounds to inhibit lipoxygenase and/or cyclooxygenase enzymes make them useful for controlling the symptoms induced by the endogenous metabolites arising from arachidonic acid in a mammalian subject. These compounds are therefore valuable in the prevention and treatment of such disease states in which the accumulation of arachidonic acid metabolites are the causative factor, e.g., allergic bronchial asthma, skin disorders, rheumatoid arthritis, osteoarthritis and thrombosis.

The activity of the compounds of the formula (IV) and their enantiomers can also be demonstrated in the standard carrageenin-induced rat foot edema test (C. A. Winter et al., Proc. Soc. Exp. Biol. III, p 544, 1962).

Thus, the compounds of formula (IV) and their enantiomers are of particular use in the treatment or alleviation of allergic or inflammatory conditions in a human subject as well in the inhibition of the cyclooxygenase and lipoxygenase enzymes.

For treatment of the various conditions described above, the compounds of formula (IV) and their enantiomers are administered to a human subject either alone, or, preferably, in combination with pharmaceutically-acceptable carriers or diluents in a pharmaceutical composition, according to standard pharmaceutical practice. A compound can be administered by a variety of conventional routes of administration including orally, parenterally and by inhalation. When the compounds are administered orally, the dose range will be from about 0.1 to 20 mg/kg body weight of the subject to be treated per day, preferably from about 0.1 to 1.0 mg/kg per day in single or divided doses. If parenteral administration is desired, then an effective dose will be from 0.1 to 1.0 mg/kg body weight of the subject to be treated per day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of formula (IV) and their enantiomers can be administered, for example, in the form of tablets, powders, lozenges, syrups or capsules, or as an aqueous solution or suspension. In the case of tablets for oral use, carriers which are commonly used include lactose and corn starch. Further, lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solute should be controlled to make the preparation isotonic.

The present invention is illustrated by the following examples. However, it should be understood that the invention is not limited to the specific details of these examples.

EXAMPLE 1

S-Camphorsulfonic Acid Salt of 3,4R-Dimethyl-5S-phenyl-2R-(3R-tetrahydropyranyl) oxazolidine Under $N_2$, at ambient temperature, racemic 3-formyltetrahydrofuran (155.5 g, 1.36 mols) was dissolved in 2 liters of $CH_2Cl_2$ (+)-Ephedrine (224.7 g, 1.36 mols) was then added portionwise over 3 minutes to the resulting mixture solution to yield a clear solution, which had warmed to 29° C., and which, after 5 minutes, became hazy due to the formation of water of reaction. After stirring an additional 15 minutes at 29° C., the mixture was warmed to 40° C. and gently refluxed for 1 hour. The reaction mixture was cooled to 25° C. and anhydrous $MgSO_4$(240 g, 2 mols) added portionwise over 3 minutes. After stirring for 1 hour, partially hydrated $MgSO_4$ was recovered by filtration with 1 liter of $CH_2Cl_2$ for wash. The combined filtrate and wash liquor was stirred at 23° C. as S-camphorsulfonic acid (316 g, 1.36 mols) was added portionwise over 1 minute, followed by isopropyl ether (3 liters) added over 10 minutes. The resulting solution, whose temperature had risen to 31° C., was stirred at 23° C. Crystallization of present title product began after 12 minutes. After stirring for up to 40 hours, crystalline title product was recovered by filtration, using 1 liter of 1:1 $CH_2Cl_2$: isopropyl ether for wash, and vacuum dried at 40° C. for 4 hours; 161.5 g; m.p. 165°-166° C. (after shrinking at 163° C.); $[alpha]_D^{23} = +76.6°$ (c=0.832, $CH_3OH$).

Recrystallization was achieved by dissolving 160.8 g of this product in 800 ml of $CH_2Cl_2$ at 35° C. Isopropyl ether (800 ml) was added over 3 minutes. Crystallization began immediately. After stirring for 18 hours at 23° C., recrystallized product was recovered and dried as above; 144.4 g; m.p. 167°-168° C. (after shrinking at 166° C.); $[alpha]_D^{23} = +77.4°$ (c=1.392, $CH_3OH$).

Analysis calculated $C_{26}H_{39}NO_6S$: C, 63.26; H, 7.96; N, 2.84. Found: C, 63.24; H, 7.79; N, 2.84.

Mother liquors and washes from these recrystallizations are combined and stripped to yield the crude S-camphorsulfonic acid salt of 3,4R-dimethyl-5S-phenyl-2R-(3S-tetrahydropyranyl) oxazolidine which is suitable for recycling to (+)-ephedrine and to racemic 3-formyltetrahydropyran starting materials.

Substituting (−)-ephedrine for (+)-ephedrine and R-camphorsulfonic acid for S-camphorsulfonic acid, the R-camphorsulfonic acid of enantiomeric 3, 4S-dimethyl-5R-phenyl- 2S-(3S-tetrahydropyranyl) oxazolidine is prepared. This product, except for sign of rotation, has physical properties identical with those of the above title product.

By the same method, substituting a molar equivalent amount of p-toluenesulfonic acid for S-camphorsulfonic acid, the p-toluenesulfonic acid salt of 3,4R-dimethyl-5S-phenyl-2R-(3R-tetrahydropyranyl) oxazolidine was prepared; m.p. 148°-149.5° C. (with gassing); $[alpha]_D^{23} = +67.1°$ (c=0.61, $CH_3OH$).

EXAMPLE 2

3,4R-Dimethyl-5S-phenyl-2R-(3R-tetrahydropyranyl)oxazolidine

Title product of Example 1 (5.55 g, 0.0112 mol) was added to a stirred mixture of 100 ml of hexane and a solution of $Na_2CO_3$ (5.25 g, 0.05 mol) in 100 ml of $H_2O$. After stirring for 1 hour, the aqueous layer was separated and washed with 50 ml of fresh hexane. The organic layers were combined, washed twice with 50 ml of $H_2O$, dried ($Na_2SO_4$) and stripped in vacuum to yield title product initially as an oil, which crystallized on standing; 2.9 g; m.p. 68°-69.5° C.; $[alpha]_D^{23} = +78.2°$ (c=0.975, $CH_3OH$).

By the same method, 3,4R-dimethyl-5R-phenyl-2S-(3S-tetrahydropyranyl)oxazolidine, of identical melting point, but opposite sign of rotation, is prepared from its R-camphorsulfonic acid salt.

By the same method, present title product was prepared from the corresponding p-toluenesulfonate salt in 96% yield.

EXAMPLE 3

3R-Formyltetrahydropyran

Title product of Example 1 (48.1 g) and $H_2O$ (1 liter) were stirred at 23° C. Dissolution was almost complete after 10 minutes and was complete after less than 1 hour. The initially observed pH was 3.21. It rose to 3.48 after 10 minutes, to 4.09 after 1 hour and 4.32 after 2 hours, where it remained constant over the ensuing 0.5 hour. After stirring for a total of 2.5 hours, the aqueous solution was extracted 1×364 ml $CH_2Cl_2$ and 3×150 ml $CH_2Cl_2$. The four organic layers were combined, dried ($MgSO_4$) and stripped to yield present title product as a colorless oil, 8.8 g; $[alpha]_D^{23} = +2.84°$ (c=0.634, $CHCl_3$).

(+)-Ephedrine is recovered from the mother liquor by basification and extraction into $CH_2Cl_2$.

Title product is prepared in like manner from the corresponding p-toluenesulfonate salt.

3S-Formyltetrahydropyran, having equal but opposite sign of rotation, is prepared in like manner from the R-camphorsulfonic acid salt or the p-toluenesulfonate salt of 3,4S-dimethyl-5R-phenyl-2S-(3S-tetrahydropyranyl)-oxazolidine.

EXAMPLE 4

5-Fluoro-6-[(3R-tetrahydropyranyl)-methylamino]-2(3H)-benzoxazolone

To a solution of 5.04 g (30.0 mmol) of 6-amino-5-fluoro-2(3H)-benzoxazolone in 100 ml methanol was added 4.04 g of 3S-formyltetrahydropyran prepared as described in the preceding Example. Then, 4.0 ml acetic acid and 1.9 g (30.2 mmol) of sodium cyanoborohydride were added to the solution and the mixture was stirred for 1.5 hours. The solvent was evaporated down and water was added to the residue. The resulting solids were collected by filtration and dried at 50° C. under vacuum. Recrystallization of the crude product from methanol afforded 4.075 g of the title compound.

IR(CH$_2$Cl$_2$): 3500, 1790, 1780 cm$^{-1}$

NMR(CDCl$_3$): 1.36–1.67 (m), 1.89 (m, 1H), 3.04 (dd, 1H, J=8, 12 Hz), 3.16 (DD, 1H, J=3.5, 12 Hz), 3.42–3.61 (m, 2H), 4.03 (m, 1H), 4.27 (m, 1H), 6.62 (d, 1H, J=7.1 Hz), 6.78 (d, 1H, J=10.3 Hz), 8.52 (br.s, 1H)

EXAMPLE 5

5-Fluoro-6-[(3S-tetrahydropyranyl)-methylamino]-2(3H)-benzoxazolone

At 24° C., glacial acetic acid (6.3 ml, 0.110 mol) was added to a stirred mixture of 6-amino-5-fluoro-2(3H)-benzoxazolone (10.55 g, 0.0628 mol) in 314 ml of methanol. This was followed by the addition of title product of the preceding Example (8.6 g, 0.075 mol). The stirred reaction slurry thinned and complete dissolution occurred after 5 minutes. After an additional 10 minutes at 23° C., solids appeared. The reaction temperature was lowered to 20° C. and, after stirring at this temperature for 1 hour, sodium cyanoborohydride (5.9 g, 0.094 mol) was added in portions over a 7 minute period so as to control the rate of gas evolution. After stirring at 20° C. for an additional 2.5 hours, the methanol was stripped in vacuo to yield methanol damp solids, which were slurried in 0.25 liters of H$_2$O at 23° C. Over a 15 minute period, the pH was adjusted from 4.3 to 7.5 by the portionwise addition of 10.4 g (0.124 mol) of NaHCO$_3$ with gas evolution controlled by the rate of addition. After stirring for 20 minutes, crude title product was recovered by filtration and dried in air; 15.3 g. To purify, the crude product was taken into 1.7 liters of methanol, clarified by filtration, the filtrate stripped to yield methanol damp solids, and 40 ml of isopropyl alcohol added. The resulting mixture was restripped to yield isopropyl alcohol damp solids which were dissolved in 50 ml of isopropyl alcohol at 80° C. on a steam bath. The bath was removed, and 125 ml of hexane added slowly to the stirred solution. The resulting thick slurry was cooled slowly to 22° C. and purified title product recovered by filtration and dried in vacuum at 40° C.; 10.3 g; m.p. 149°–151° C.; [alpha]$_D^{23}$= +16.01 (c=0.531, CH$_3$OH).

PREPARATION A

6-Amino-5-fluoro-2(3H)-benzoxazolone

A.1 4-Fluoro-2-nitrophenol

To a mechanically stirred solution of 400 ml concentrated nitric acid, at 0° C., was added dropwise a solution of 4-fluorophenol (204 g, 1.8 mole) in acetic acid (200 ml) over 2 hours. Stirring was continued for another 2 hours at 5° C. The reaction mixture was poured onto ice, and the resulting yellow solids were collected and washed with water. The solids were recrystallized from methanol-water (5:1) to afford 198 g of the title compound. The NMR spectrum showed absorption at 7.17 (dd, 1H, J=9, 5 Hz), 7.44–7.52 (m, 1H) and 7.80 (dd, 1H, J=8, 3 Hz).

A.2 2-Amino-4-fluorophenol

To a solution of 4-fluoro-2-nitrophenol (48.3 g, 0.30 mole) in 300 ml ethanol was added 0.24 g platinum oxide under nitrogen atmosphere. The mixture was hydrogenated with a Parr shaker for 8 hours at 45 psi. The catalyst was filtered off and the filtrate was concentrated to leave 40.5 g of the title compound as a brown powder. The NMR spectrum showed absorption at 4.79 (br.s, 2H), 6.11 (m, 1H), 6.36 (dd, 1H, J=11, 3 Hz), 6.53 (dd, 1H, J=5, 9 Hz) and 8.89 (s, 1H).

A.3 5-Fluoro-2(3H)-benzoxazolone

To a solution of 2-amino-4-fluorophenol (40.5 g, 0.32 mole) in 400 ml tetrahydrofuran, at 0° C., was added dropwise trichloromethyl chloroformate (44.8 ml, 0.32 mole). The reaction mixture was allowed to warm up to room temperature. Stirring was continued for 2 hours. Then, the reaction mixture was poured onto ice and the organic substance was extracted with ethyl acetate (500 ml×3). The combined extracts were washed with saturated sodium bicarbonate solution, dried over magnesium sulfate and concentrated to yield 44.3 g of the title compound as brown solids.

The NMR spectrum showed absorption at 6.86–6.90 (m, 1H), 7.01 (dd, 1H, J=8 3 Hz), 7.30 (dd, 1H, J=9, 5 Hz) and 11.82 (br.s, 1H).

A.4 5-Fluoro-6-nitro-2(3H)-benzoxazolone

To a stirred solution of 300 ml concentrated nitric acid, at room temperature, was added portionwise 73.2 g (0.48 mole) of 5-fluoro-2(3H)-benzoxazolone. The reaction mixture was warmed to 50° C., and was stirred for 4 hours. After cooling, the reaction mixture was poured onto ice. The precipitate which formed was collected, washed with water, and dried to give 72.8 g of the title compound as a brown powder: m.p. 207°–209° C.

IR (Nujol): 3300, 1810, 1780, 1630 cm$^{-1}$

NMR: 7.35 (d, 1H, J=11.0 Hz), 8.16 (d, 1H, J=6.6 Hz), 12.6 (br.s, 1H)

A.5 6-Amino-5-fluoro-2(3H)-benzoxalone

To a solution of 5-fluoro-6-nitro-2(3H)-benzoxazolone (20 g, 0.1 mole) in 300 ml tetrahydrofuran was added 2 g palladium carbon (5%) under nitrogen atmosphere. The mixture was hydrogenated with a Parr shaker for 10 hours at 45 psi. The precipitate which resulted from hydrogenation was redissolved by adding tetrahydrofuran. The catalyst was removed by filtration and the filtrate was concentrated to give 18.1 g of the title compound as a brown solid: m.p. 180°–182° C. (dec.).

IR (Nujol): 3400, 3280, 1750, 1630 cm$^{-1}$

NMR: 4.93 (br.s, 2H), 6.71 (d, 1H, J=7.3 Hz), 6.84 (d, 1H, J=10 Hz), 11.2 (br.s, 1H)

PREPARATION B

Racemic 5-Formyltetrahydropyran

Under N$_2$, a 25 gallon, glass-lined, water-jacketed, stirred reactor was charged with 10% Pd/C (298 g, 50% water-wet), 11.9 Kg of 5-formyl-3, 6-dihydro-5-formyl(2H)-pyran and 60 liters of tetrahydrofuran. Without stirring, the reactor was purged 3×20 psig of N$_2$ and then 3×20 psig of H$_2$, then pressurized to 50 psig with H$_2$. With water jacket and internal temperature at 23°–24° C., stirring was initiated. The pressure of H$_2$ was maintained at 40–50 psig and the temperature, which rose no higher than 32° C., maintained by the 23°–24° C. water jacket. After stirring for 2.5 hours, by which time H$_2$ uptake was complete, the reactor was purged 3×20 psig of N$_2$ and the catalyst removed by filtration under a N$_2$ pressure of 10 psig. The filtrate was stripped to dryness to yield 11.0 Kg (92%) of title product of excellent quality according to its $^1$H-NMR in CHCl$_3$: 1.45–1.91 (m, 4H), 2.34–2.43 (m, 1H), 3.47 (d.d.d., 1H, J=11.5, 7.6, 3.7 Hz), 3.63 (d.d.d., 1H, J=11.3, 6.5, 3.9 Hz), 3.72 (d.d., 1H, J=11.7, 6.8 Hz), 3.88 (d.d., 1H, J=11.7, 3.2 Hz), 9.62 (s, 1H).

We claim:

1. A process for the preparation of an optically active 3-formyltetrahydropyran of the absolute stereochemical formula

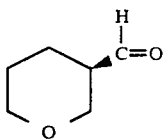
(Ia)

or

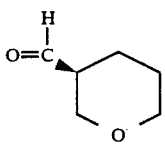
(Ib)

which comprises the steps of:
(a) reacting racemic 3-formyltetrahydropyran in a reaction inert solvent either with (+)-ephedrine to form a mixture of diastereomeric oxazolidines of the formulas:

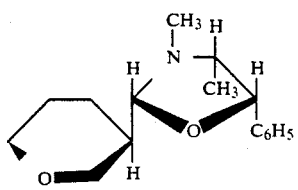
(IIa)

and

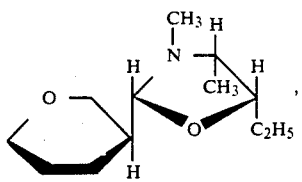
(IIIa)

or with (−)-ephedrine to form a mixture of diastereomeric oxazolidines of the formulas:

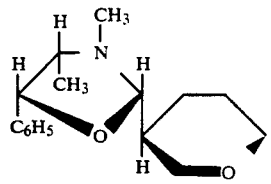
(IIb)

and

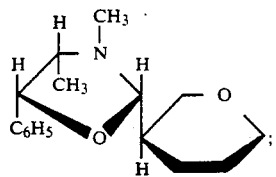
(IIIb)

(b) separating the diastereomeric oxazolidine of the formula (IIa) or (IIb) from its respective mixture in the form of a crystalline, acid addition salt; and
(c) hydrolyzing in water the resulting diastereomeric salt of the oxazolidine of formula (IIa) or (IIb) to form, respectively, said optically active 3-formyltetrahydropyran of the formula (Ia) or of the formula (Ib).

2. A process of claim 1 for the preparation of the optically active 3-formyltetrahydropyran of the formula (Ia).

3. A process of claim 2 wherein the acid addition salt is the 1S-camphorsulfonic acid salt.

4. A process of claim 2 wherein the acid addition salt is the p-toluenesulfonic acid salt.

5. A compound of the absolute stereochemical formula

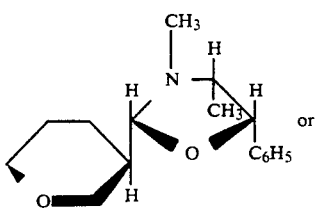
(IIa)

or

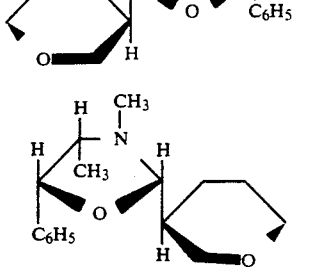
(IIb)

or an acid addition salt thereof.

6. The compound of claim 5 of the formula (IIa).

7. The compound of claim 6 in the form of its 1S-camphorsulfonic acid salt.

8. The compound of claim 6 in the form of its p-toluenesulfonic acid salt.

* * * * *